(12) United States Patent
Lai et al.

(10) Patent No.: US 7,241,312 B2
(45) Date of Patent: Jul. 10, 2007

(54) SILICONE INTRAOCULAR LENS WITH BLUE LIGHT ABSORPTION PROPERTIES

(75) Inventors: Yu-Chin Lai, Pittsford, NY (US); Dominic V. Ruscio, Webster, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 5 days.

(21) Appl. No.: 11/235,497

(22) Filed: Sep. 26, 2005

(65) Prior Publication Data

US 2006/0020337 A1    Jan. 26, 2006

Related U.S. Application Data

(62) Division of application No. 10/657,781, filed on Sep. 8, 2003.

(51) Int. Cl.
*A61F 2/16*  (2006.01)
*C09K 19/52* (2006.01)

(52) U.S. Cl. ...................... 623/6.62; 351/163

(58) Field of Classification Search ............. 623/66.11, 623/6.62, 6.6, 6.57, 6.56; 427/2.24; 526/259, 526/326, 346, 279; 542/588; 525/100, 106; 351/159, 160 R, 162–166; 556/425, 443; 528/25, 31
See application file for complete search history.

(56) References Cited

U.S. PATENT DOCUMENTS

| | | | |
|---|---|---|---|
| 4,468,229 A * | 8/1984 | Su ................................. 8/507 |
| 5,470,932 A | 11/1995 | Jinkerson |
| 5,528,322 A | 6/1996 | Jinkerson |
| 5,543,504 A | 8/1996 | Jinkerson |
| 5,596,025 A * | 1/1997 | Oxman et al. ............... 523/109 |
| 5,662,707 A | 9/1997 | Jinkerson |
| 5,891,931 A | 4/1999 | Leboeuf et al. |
| 6,015,842 A | 1/2000 | Leboeuf et al. |
| 6,187,042 B1 * | 2/2001 | Sheets et al. ............... 623/6.62 |
| 6,353,069 B1 | 3/2002 | Freeman et al. |
| 2002/0028330 A1 * | 3/2002 | Patel et al. .................. 428/336 |

FOREIGN PATENT DOCUMENTS

| EP | 1293541 A2 | 3/2003 |
|---|---|---|
| JP | 200089171 | 3/2000 |

* cited by examiner

*Primary Examiner*—David J. Isabella

(57) ABSTRACT

A process for producing silicone intraocular lenses (IOLs) capable of absorbing blue light. Intraocular lenses so produced block blue light from reaching the retina of an eye implanted with the IOL. By blocking blue light from reaching the retina, the IOL thereby prevents potential damage to the retina.

8 Claims, No Drawings

SILICONE INTRAOCULAR LENS WITH BLUE LIGHT ABSORPTION PROPERTIES

CROSS-REFERENCE OF RELATED APPLICATION

This application is a divisional of Ser. No. 10/657,781, filed Sep. 8, 2003.

FIELD OF THE INVENTION

The present invention relates to a process for making silicone intraocular lenses with blue light absorption properties. More particularly, the present invention relates to a process for reacting a silicone intraocular lens with an ethyleneically unsaturated yellow dye to produce an intraocular lens capable of blocking blue light.

BACKGROUND OF THE INVENTION

Since the 1940's optical devices in the form of intraocular lens (IOL) implants have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lens implants was poly(methyl methacrylate), which is a rigid, glassy polymer.

Softer, more flexible IOL implants have gained in popularity in more recent years due to their ability to be compressed, folded, rolled or otherwise deformed. Such softer IOL implants may be deformed prior to insertion thereof through an incision in the cornea of an eye. Following insertion of the IOL in an eye, the IOL returns to its original pre-deformed shape due to the memory characteristics of the soft material. Softer, more flexible IOL implants as just described may be implanted into an eye through an incision that is much smaller, i.e., less than 4.0 mm, than that necessary for more rigid IOLs, i.e., 5.5 to 7.0 mm. A larger incision is necessary for more rigid IOL implants because the lens must be inserted through an incision in the cornea slightly larger than the diameter of the inflexible IOL optic portion. Accordingly, more rigid IOL implants have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in artificial IOL implants. Mazzocco, U.S. Pat. No. 4,573,998, discloses a deformable intraocular lens that can be rolled, folded or stretched to fit through a relatively small incision. The deformable lens is inserted while it is held in its distorted configuration, then released inside the chamber of the eye, whereupon the elastic property of the lens causes it to resume its molded shape. As suitable materials for the deformable lens, Mazzocco discloses polyurethane elastomers, silicone elastomers, hydrogel polymer compounds, organic or synthetic gel compounds and combinations thereof.

In recent years, blue light (400-500 nm) has been recognized as being potentially hazardous to the retina. Accordingly, yellow dyes to block blue light have been used in foldable intraocular lenses, in conjunction with ultraviolet light absorbers, to avoid potential damaging effects. Freeman et al., U.S. Pat. No. 6,353,069, disclose high refractive index copolymers comprising two or more acrylate and/or methacrylate monomers with aromatic groups. Ophthalmic devices made of the copolymers may also include colored dyes, such as the yellow dyes disclosed in U.S. Pat. No. 5,470,932. Such materials exhibit sufficient strength to allow devices made of them, such as intraocular lenses, to be folded or manipulated without fracturing.

Because of shortcomings in the properties of many soft, flexible materials used in the manufacture of ophthalmic devices, such as the formation of water vacuoles or "glistenings", and low refractive index, which requires a lens to be relatively thick in order to provide a lens of proper refractive power, new materials and methods of manufacturing of ophthalmic devices are needed.

SUMMARY OF THE INVENTION

Soft, foldable, high refractive index, silicone intraocular lenses (IOLs) capable of absorbing blue light are prepared in accordance with the present invention through a coating process using a reactive yellow dye solution having blue light blocking properties. The blue light absorbing IOLs produced in accordance with the present invention protect an eye's retina from potentially damaging blue light and thereby possibly providing protection from macular degeneration.

Blue light blocking silicone IOLs of the present invention are produced by exposing a semi-finished silicone IOL to an ethyleneically unsaturated yellow dye-containing solution and allowing the same to undergo a hydrosilation reaction. Such production process yields silicone IOLs with blue light absorbing properties. By absorbing blue light, the IOL serves to block blue light from reaching and potentially damaging the retina of an eye implanted with the IOL. Silicone IOLs so produced are transparent, relatively high in elongation and relatively high in refractive index.

Accordingly, it is an object of the present invention to provide a process for the production of silicone IOLs capable of absorbing blue light.

Another object of the present invention is to provide a process for the production of silicone IOLs having relatively high refractive indices and good clarity.

Another object of the present invention is to provide a process for the production of silicone IOLs that are flexible.

Still another object of the present invention is to provide biocompatible silicone IOLs capable of absorbing blue light.

These and other objectives and advantages of the present invention, some of which are specifically described and others that are not, will become apparent from the detailed description and claims that follow.

DETAILED DESCRIPTION OF THE INVENTION

The present invention relates to a novel process for the production of high refractive index silicone IOLs capable of absorbing blue light and thereby blocking blue light from reaching the retina of an eye implanted with the IOL. Silicone IOLs of the present invention are produced by allowing a semi-finished silicone IOL to react with an ethyleneically unsaturated dye through a hydrosilation reaction. The subject process for treating silicone IOLs is relatively simple and produces biocompatible silicone IOLs capable of absorbing blue light.

A "semi-finished" silicone IOL for purposes of the present invention, is a silicone IOL having free hydrosilyl groups. By dipping a semi-finished silicone IOL in a weak solvent, such as for example but not limited to methylene chloride, containing a one or more reactive dyes, such as a reactive yellow dye, and one or more platinum catalysts, followed by thermal treatment of the IOL in an oven at a low temperature, preferably less than approximately 100° C. for a relatively short period of time, preferably less than several hours and more preferably less than approximately 30 minutes, a quantitative amount of dye can be incorporated into or coat the IOL. There are several platinum catalysts or catalyst systems suitable for the hydrosilation reaction of the present invention, depending on the reaction temperature and kinetics desired. For example, platinum (3 to 3.5%)-divinyltetramethyldisiloxane complex is suitable for use in a room temperature reaction. Platinum (3 to 3.5%)-cyclovinylmethylsiloxane complex is suitable for use in a reaction at a moderate temperature of 50 to 100° C. The reaction kinetics can be regulated through the concentration of the catalyst and through the addition of various amounts of one or more inhibitors. Suitable inhibitors include for example but are not limited to 1,3-divinyltetramethyldisiloxane and 1,3,5,7-tetramethyl-1,3,5,7-tetravinyl cyclosiloxane. Such inhibitors may be present in the catalyst complex. The chemical reaction that takes place as a result of this process is illustrated below in Reaction Scheme 1.

REACTION SCHEME 1

As depicted above in Reaction Scheme 1, Si—H represents the free hydrosilyl groups of a "semi-finished" silicone IOL, and $H_2C=CR_1R_2$ represents a reactive yellow dye. Here, $R_1$ can be H or $CH_3$ and $R_2$ is a group containing other functional groups as well as functional groups responsible for yellow color. The reactive yellow dye can have for example, but is not limited to the following ethylenically unsaturated groups: vinyl, allyl, acrylate, methacrylate, acrylamide, methacrylamide, fumarate, maleate, itaconate, styrene, nitrile and the like. Depending on the particular solvent and the concentration of reactive yellow dyes in the solvent, the reactive yellow dye can penetrate into the polymer matrix of the lens body, as well as, partially or completely coat the lens surface.

Reactive dyes useful in the manufacture of flexible, high refractive index silicone IOLs capable of absorbing blue light, may be prepared through a process of multiple chemical reaction steps. This process includes a step for forming a blue light absorbing functional group, i.e., a dye, such as for example but not limited to a diazo coupling for azo dye formation. The process also Includes a step to incorporate the compound with a dye functional group and a reagent that is ethylenically unsaturated. For example, a reactive azo yellow dye having two ethylenically unsaturated groups can be prepared by reacting a yellow dye having two alcohol groups with an acid chloride or an isocyanate having an ethylenically unsaturated group. Such is depicted in Reaction Schemes 2 through 3 wherein a yellow dye, N,N-bis-(2-hydroxyethyl)-(4-phenylazo) aniline (Solvent Yellow 58), synthesized in accordance with the procedure of Example 1 below, is used as an example not intended to be limiting.

REACTION SCHEME 2
Synthesis of N, N-bis-(2-allylcarbamatoethyl)-
(4'-phenylazo) aniline as described in Example 2 below.

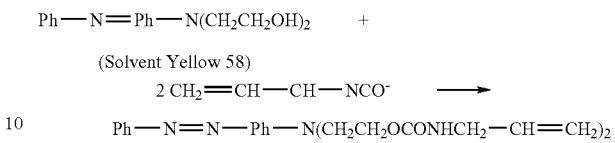

Here, "Ph" represents either $C_6H_5$ or $C_5H_4$, as appropriate.

REACTION SCHEME 3
Synthesis of 3-butenoate (vinylacetate) of
Solvent Yellow 58 as described in Example 3 below.

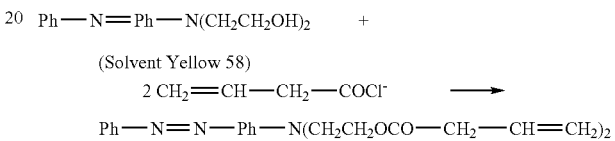

Alternatively, a reactive yellow dye with one ethylenically unsaturated group useful in accordance with the present invention, such as for example but not limited to N-2-[3'-(2"-methylphenylazo)-4'-hydroxyphenyl]ethyl vinylacetamide, represented below in Formula 1, Formula 1

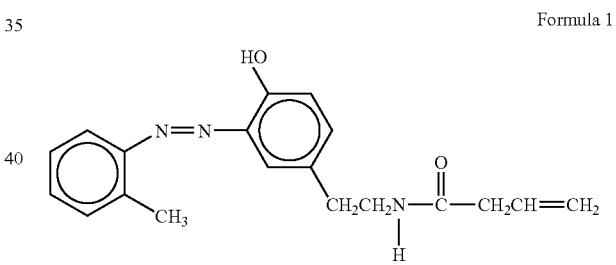

can be prepared by first reacting vinylacetyl chloride with 4-aminoethylphenol to give 4-vinylacetamidoethyl phenol, which is then coupled with the diazonium salt of toluidine as described in more detail below in Example 4.

The process of the present invention for preparing flexible, high refractive index silicone IOLs with blue light absorption properties is described in still greater detail in the Examples provided below.

EXAMPLE 1

Synthesis of N,N-bis-(2-hydroxyethyl)-(4-phenylazo) aniline (Solvent Yellow 58)

The synthesis of N,N-bis-(2-hydroxyethyl)-(4-phenylazo) aniline is accomplished by coupling the diazonium salt of aniline with N-phenyl diethanolamine. A detailed procedure is also described in D. L. Jinkerson, U.S. Pat. No. 5,470,932, incorporated herein in its entirety by reference.

EXAMPLE 2

Synthesis of N,N-bis-(2-allylcarbamatoethyl)-(4'-phenylazo)aniline

A 1000-mL 3-neck, round bottom flask connected with a reflux condenser and a drying tube, is charged with 250 mL of methylene chloride, 5.7 grams (0.02 mole) of N,N-bis-(2-hydroxyethyl)-(4-phenylazo)aniline, 3.28 g of allyl isocyanate (0.04 mole) (Aldrich Chemical, Inc., Milwaukee, Wis.) and 0.014 g of dibutyltin dilaurate (Aldrich Chemical). The mixture is heated and refluxed overnight under vigorous stirring. The mixture is then checked with infrared spectroscopy and no residual isocyanate peak is found indicating the reaction is complete. The mixture is concentrated using a rotavapor. High performance liquid chromatography (HPLC) analysis indicates only one major product. The product is then passed through silica gel chromatography to give final purified product with a yield of at least 80 percent. The product is identified by nuclear magnetic resonance (NMR) and Mass Spectroscopy.

EXAMPLE 3

Synthesis of N,N-bis-(2-vinylacetoxyethyl)-(4'-phenylazo)aniline

A 1000-mL 3-neck, round bottom flask connected with a reflux condenser and a drying tube, is charged with 250 mL of methylene chloride, 5.7 grams (0.02 mole) of N,N-bis-(2-hydroxyethyl)-(4-phenylazo) aniline and 4.04 grams of triethylamine (0.04 mole). The contents are chilled with an ice bath. Through a dropping funnel, 4.18 g (0.04 mole) of vinylacetyl chloride is added into the flask over a period of 30 minutes. The ice bath is then removed and the contents are continuously stirred overnight. The mixture is then filtered and then condensed using a rotavapor. HPLC analysis indicates only one major product. The product is then passed through silica gel chromatography to give a final purified product with a yield of at least 80 percent. The product is identified by NMR and Mass Spectroscopy.

EXAMPLE 4

Synthesis of N-2-[3'-2"-methylphenylazo)-4'-hydroxyphenyl]ethyl vinylacetamide

N-2-[3'-(2"-methylphenylazo)-4'-hydroxyphenyl]ethyl vinylacetamide can be made in two steps. The first step is the formation of 4-vinylacetamidoethyl phenol. The second step is the coupling of azonium salt of toluidine with the phenol to give the product.

Step 1. Synthesis of 4-vinylacetamidoethyl phenol.

A 1000-mL 3-neck, round bottom flask connected with a reflux condenser and a drying tube, is charged with 250 mL of methylene chloride, 5.48 grams (0.04 mole) 4-aminoethylphenol and 4.04 grams (0.04 mole) triethylamine. The contents are chilled with an ice bath. Through a dropping funnel, 4.18 g (0.04 mole) of vinylacetyl chloride is added into the flask over a period of 30 minutes. The ice bath is then removed and the contents are continuously stirred overnight. The mixture is then filtered and then condensed using a rotavapor. High performance liquid chromatography (HPLC) analysis indicates only one major product. The product is then passed through silica gel chromatography to give a final purified product with a yield of at least 80 percent. The product is identified by NMR and Mass Spectroscopy.

Step 2. Coupling of Product from Step 1 with Toluidine Diazonium Salt.

The procedure is about the same as that described in D. L. Jinkerson, U.S. Pat. No. 5,470,932, Example 1, second half. The difference is that 4-vinylacetamidoethyl phenol is used to replace the acrylamidoethyl phenol. The product is identified by NMR and Mass Spectroscopy.

EXAMPLE 5

Preparation of Yellow Dye Solution for Coating of an IOL

Solutions containing 0.1, 0.5, 1, 2 and 5 weight percent of the yellow dye of Example 4 in methylene chloride are prepared. To these solutions, platinum-cyclovinylmethylsiloxane complex (Gelest, Inc., Tullytown, Pa.) at 1% of the weight of the yellow dye is also added.

EXAMPLE 6

Coating of Silicone Intraocular Lenses

Ten (10) freshly thermally cured SoFlex™ Model LI61U (Bausch & Lomb, Incorporated, Rochester, N.Y.) lenses are submerged into each coating solution as described in Example 3 for 30, 60 and 120 minutes. The lenses are then removed from the coating solutions and air dried. The lenses are then placed in an oven at 80 to 90° C. for an hour. These lenses are then subjected to standard processing to get the final finished product.

Model LI61U lenses are silicone IOLs derived from components consisting of a vinyl terminated polydimethyl-co-diphenyl siloxane, silicon-based reinforcing resins with vinyl groups, and an oligomer with multi hydrosilane units. Model L161 U silicone lenses have excess free hydrosilane groups after curing.

EXAMPLE 7

Selection of Yellow Dye Concentration and Coating Conditions

Run ultraviolet (UV) and visible absorption spectroscopy of coated lenses before and after processing. Select the yellow dye concentration and residence time of lens in dye solution based on the visible light absorption of the process lenses between 400-500 nm. Conditions, which give about or less than 50% transmittance and maintenance of lens power/cosmetics are chosen for further coating studies, followed by optimization of conditions.

Soft, foldable, relatively high refractive index of approximately 1.42 or greater, relatively high elongation of approximately 100 percent or greater, silicone IOLs with blue light absorption properties are synthesized through the process of the present invention. Suitable catalysts for use in the process of the present invention include but are not limited to platinum (3-3.5%)-divinyltetramethyldisiloxane complex and platinum (3-3.5%)-cyclovinylmethylsiloxane complex.

The silicone IOLs produced as described herein have the flexibility required to allow the same to be folded or deformed for insertion into an eye through the smallest possible surgical incision, i.e., 3.5 mm or smaller. It is unexpected that the subject silicone IOLs described herein could possess the ideal physical properties disclosed herein. The ideal physical properties of the subject silicone IOLs are unexpected because changes in mechanical properties such as modulus, percent elongation and tear strength can occur upon addition of the reactive dye functional groups.

Silicone IOLs treated using the process of the present invention can be of any design capable of being rolled or folded for implantation through a relatively small surgical incision, i.e., 3.5 mm or less. Such IOLs may be manufactured to have an optic portion and haptic portions made of the same or differing materials. Once the material(s) are selected, the same may be cast in molds of the desired shape, cured and removed from the molds. After such molding, the IOLs are treated in accordance with the process of the present invention and then cleaned, polished, packaged and sterilized by customary methods known to those skilled in the art.

In addition to IOLs, the process of the present invention is also suitable for use in the production of other medical or ophthalmic devices such as contact lenses, keratoprostheses, capsular bag extension rings, corneal inlays, corneal rings and like devices.

Silicone IOLs manufactured using the process of the present invention are used as customary in the field of ophthalmology. For example, in a surgical cataract procedure, an incision is placed in the cornea of an eye. Through the corneal incision the cataractous natural lens of the eye is removed (aphakic application) and an IOL is inserted into the anterior chamber, posterior chamber or lens capsule of the eye prior to closing the incision. However, the subject ophthalmic devices may likewise be used in accordance with other surgical procedures known to those skilled in the field of ophthalmology.

While there is shown and described herein a process for producing silicone IOLs with blue light absorption properties, it will be manifest to those skilled in the art that various modifications may be made without departing from the spirit and scope of the underlying inventive concept and that the same is not limited to particular processes and structures herein shown and described except insofar as indicated by the scope of the appended claims.

We claim:

1. An intraocular lens comprising:
   a coating that consists essentially of at least one reactive azo dye so that said intraocular lens has blue light absorption properties, wherein said at least one reactive azo dye reacts with a semi-finished silicone intraocular lens upon heating and is covalently attached to said intraocular lens.

2. The intraocular lens of claim 1 wherein said reactive azo dye has at least an ethylenically unsaturated group, which is selected from the group consisting of vinyl, allyl, acrylate, methacrylate, acrylamide, methacrylamide, fumarate, maleate, itaconate, styrene and nitrile.

3. The intraocular lens of claim 1 wherein said reactive azo dye is a reactive yellow dye.

4. The intraocular lens of claim 1 wherein said reactive azo dye is selected from the group consisting of N, N-bis-(2-allylcarbamatoethyl)-(4'-phenylazo)aniline and N, N-bis-(2-vinylacetoxyethyl)-(4'-phenylazo)aniline and N-2-[3'-(2"-methylphenylazo)-4'-hydroxyphenyl]ethyl vinylacetamide.

5. The intraocular lens of claim 1 wherein said reactive azo dye undergoes a hydrosilation reaction with said intraocular lens.

6. The intraocular lens of claim 1 wherein said reactive azo dye penetrates into the polymer matrix of said intraocular lens.

7. The intraocular lens of claim 1 wherein said reactive azo dye partially or completely coats the surface of said intraocular lens.

8. The intraocular lens of claim 1 further comprising platinum.

* * * * *